(12) United States Patent
Stewart et al.

(10) Patent No.: US 6,979,822 B1
(45) Date of Patent: Dec. 27, 2005

(54) CHARGED PARTICLE BEAM SYSTEM

(75) Inventors: Diane K. Stewart, Ipswich, MA (US); W. Ralph Knowles, Newbury, MA (US); Brian T. Kimball, Georgetown, MA (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 10/801,981

(22) Filed: Mar. 16, 2004

Related U.S. Application Data

(63) Continuation-in-part of application No. 10/665,398, filed on Sep. 18, 2003, now abandoned, and a continuation-in-part of application No. 10/330,691, filed as application No. 60/411,699 on Sep. 18, 2002.

(51) Int. Cl.[7] .................. H01J 37/244; H01J 37/28; H01J 37/252; G01N 23/00
(52) U.S. Cl. .................. 250/310; 250/306; 250/307; 250/309; 250/311; 250/396 R; 250/397; 250/398; 250/399; 250/492.3; 250/505.1
(58) Field of Search .................. 250/310, 311, 397, 250/399, 492.3, 306, 307, 309, 396 R, 398, 250/505.1

(56) References Cited

U.S. PATENT DOCUMENTS

| | | | |
|---|---|---|---|
| 4,249,077 A | | 2/1981 | Crawford |
| 4,601,211 A | * | 7/1986 | Whistler .................. 73/863.33 |
| 5,396,067 A | * | 3/1995 | Suzuki et al. .................. 250/310 |
| 5,578,821 A | | 11/1996 | Meisberger et al. |

(Continued)

FOREIGN PATENT DOCUMENTS

| | | |
|---|---|---|
| JP | 05-174768 | 7/1993 |
| WO | WO 2004/059691 A1 | 7/2004 |

OTHER PUBLICATIONS

C.K. Crawford, Change Neutralization Using Very Low Energy Ions, Scanning Electron Microscopy, 1979, II, SEM INc., USA.

Albert Folch et al., High Vacuum Versus, "Environmental" Electron Beam Deposition, Jul./Aug., 1996, B 14(4), pp. 2609-2614, J. Vac. Sci.

Yukinori Ochiai, Electron-Beam-Induced Deposition of Copper with Low Resistivity, Nov./Dec. 1996, B 14(6), pp. 3887-3891, J. Vac. Sci. Technol.

Witold Slowko and Herbert Prasol, "Micro-Sphere Plate as an Electron Detector at Low Vacuum." Vacuum, vol. 67, (2002) pp. 191-198.

(Continued)

*Primary Examiner*—John R. Lee
*Assistant Examiner*—Bernard E. Souw
(74) *Attorney, Agent, or Firm*—Michael O. Scheinberg

(57) ABSTRACT

A charged particle beam system uses an ion generator for charge neutralization. In some embodiments, the ion generator is configured to maintain an adequate gas pressure at the ion generator to generate ions, but a reduced pressure in the remainder of the vacuum chamber, so that another column can operate in the chamber either simultaneously or after an evacuation process that is much shorter than a process that would be required to evacuate the chamber from the full pressure required at the ion generator. The invention is particularly useful for repair of photolithography masks in a dual beam system.

26 Claims, 9 Drawing Sheets

U.S. PATENT DOCUMENTS

| | | | |
|---|---|---|---|
| 5,986,264 A * | 11/1999 | Grunewald | 250/310 |
| 6,172,363 B1 | 1/2001 | Shinada et al. | |
| 6,184,525 B1 * | 2/2001 | Van Der Mast | 250/310 |
| 6,365,896 B1 | 4/2002 | Van der Mast | |
| 6,525,317 B1 | 2/2003 | Yang | |
| 6,538,254 B1 | 3/2003 | Tomimatsu et al. | |
| 6,590,210 B1 * | 7/2003 | Essers | 250/310 |
| 6,707,041 B2 * | 3/2004 | Essers | 250/310 |
| 6,781,124 B2 | 8/2004 | Hayn | |
| 2003/0010913 A1 * | 1/2003 | Essers | 250/310 |

OTHER PUBLICATIONS

M. Jacka, M. Zadrazil and F. Lopour, "A Differentially Pumped Secondary Electron Detector for Low-Vacuum Scanning Electron Microscopy," Scanning, vol. 25, (2003) pp. 243-246.

Witold Slowko, "Secondary Electron Detector with a Micro-Porous Plate for Environmental SEM," Vacuum, vol. 63, (2001) pp. 457-461.

* cited by examiner

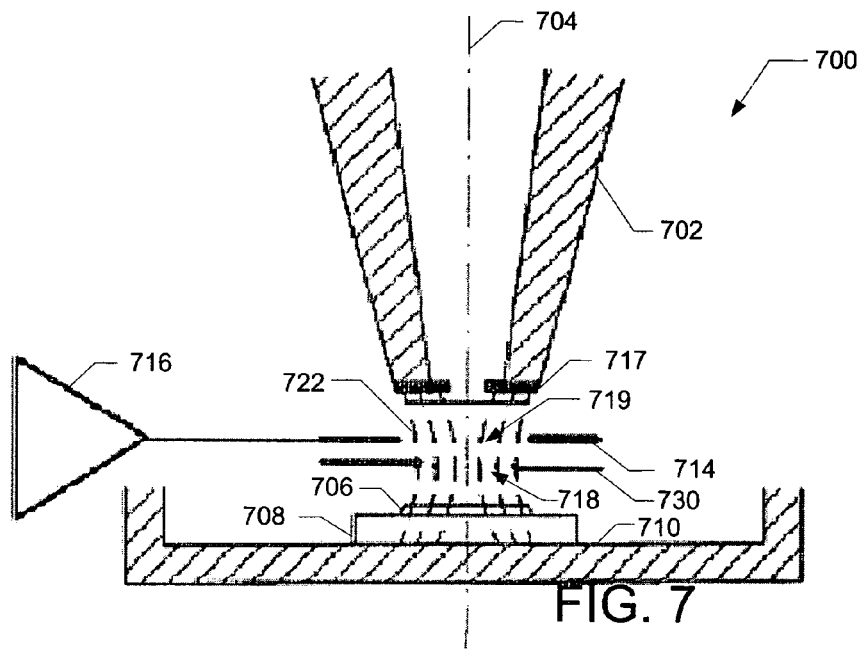
FIG. 7
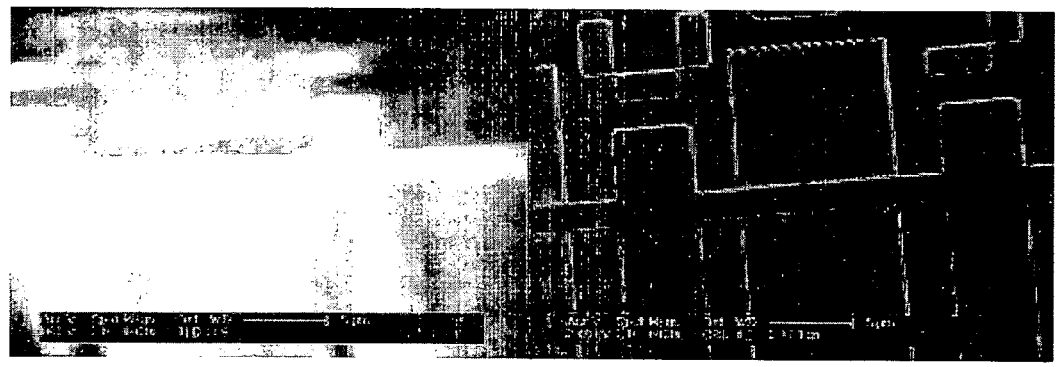
FIG. 4A
FIG. 4B

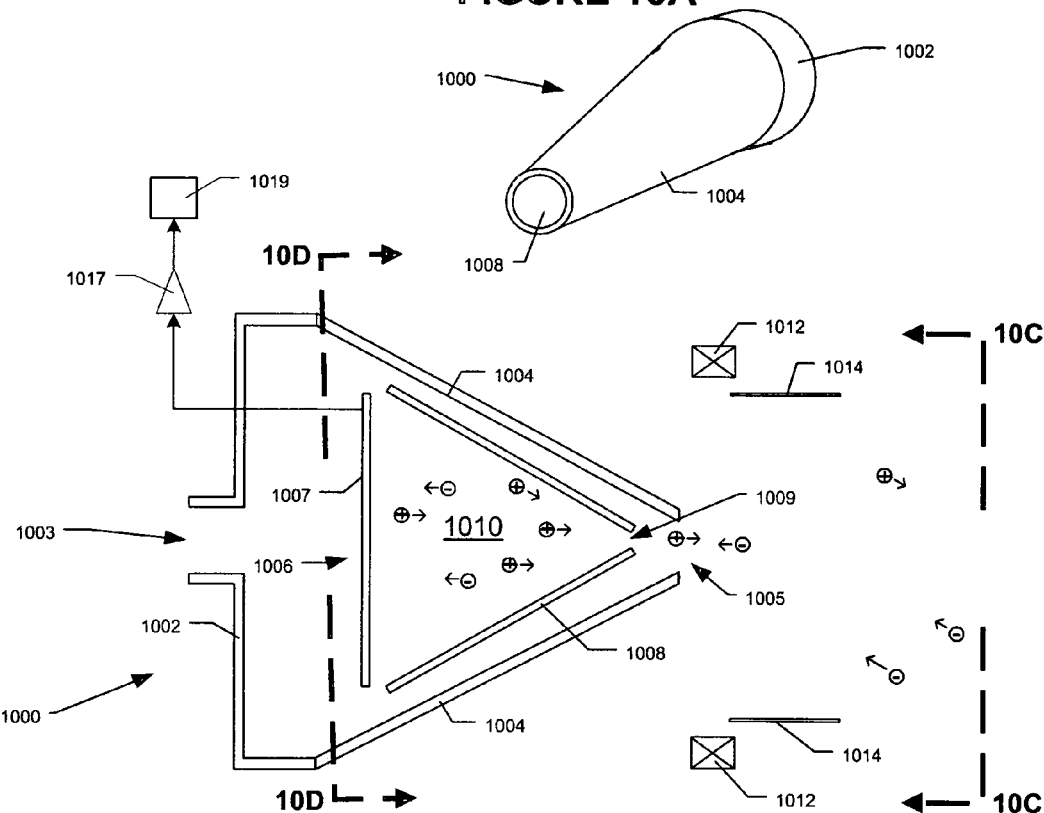
FIGURE 10A
FIGURE 10B
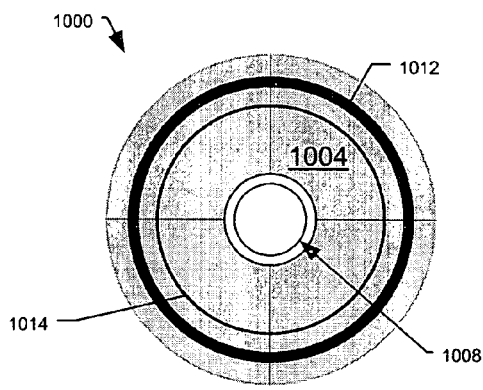
FIGURE 10C
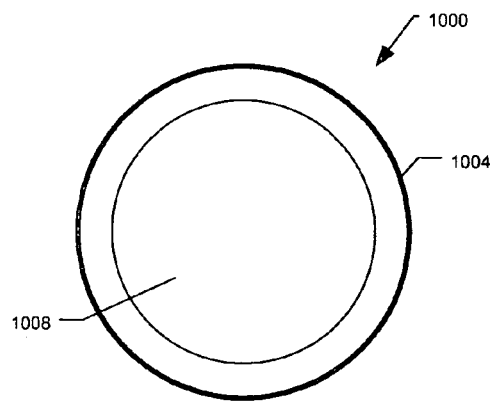
FIGURE 10D

CHARGED PARTICLE BEAM SYSTEM

This application is a continuation-in-part of U.S. patent application Ser. No. 10/665,398, filed on Sep. 18, 2003, now abandoned which is hereby incorporated by reference, which claims priority from U.S. Prov. Pat. App. No. 60/411,699, filed Sep. 18, 2002, and which is a continuation-in-part of U.S. patent application Ser. No. 10/330,691, filed on Dec. 27, 2002 now abandoned.

TECHNICAL FIELD OF THE INVENTION

The present invention relates to the field of charged particle beam tools for forming, altering and viewing microscopic structures.

BACKGROUND OF THE INVENTION

Photolithography is a process that is used to create small structures, such as integrated circuits and micromachines. The photolithography process entails exposing a radiation-sensitive substance, called photoresist, to a pattern of light or other radiation. The pattern is typically created by passing the radiation through a mask, that is, a substrate having a pattern on the surface. The pattern blocks some of the radiation or changes its phase to create exposed and unexposed areas on the radiation-sensitive material. The size of the structure that can be produced is limited by the wavelength of radiation used; shorter wavelengths can produce smaller structures.

As photolithography processes are called upon to produce ever-smaller structures, lithography systems are being developed that use smaller wavelengths of radiation, including infrared and even x-ray radiation. (The terms "light" and "photolithography" are used in a general sense to also include radiation other than visible light.) Photolithography Systems are now being developed that can produce structures having dimensions of 70 nm and smaller. Such structures can be fabricated using light having a wavelength of 193 nm or 157 nm. Some photolithography masks for such short wavelengths use a reflective, rather than a transmissive, pattern on the mask because the mask substrate is not sufficiently transparent to such radiation of short wavelengths. In such masks, radiation is reflected from the mask onto the photoresist.

A photolithography mask must be free of imperfections if the mask is to accurately produce the desired exposure pattern. Most newly fabricated masks have defects such as missing or excess pattern material. Before such masks can be used, the defects are repaired, often by using a charged particle beam system. Dual beam systems that include an ion beam and an electron beam can be used in mask repair. The ion beam is used to etch away excess material on the mask to deposit material onto the mask, or to form images of the mask. The electron beam is also used to form images of the mask and sometimes to deposit or etch material. When a charged particle beam is applied to a mask, which is typically fabricated on an insulating substrate, electrical charge tends to accumulate on the substrate. The electric charge adversely affects the operation of the charged particle beam by affecting the shape and positioning of the beam spot.

One method of neutralizing or reducing accumulated charge entails using an electron flood gun to direct electrons at a positively charged substrate. Such a system is described, for example in U.S. Pat. No. 4,639,301 to Doherty et al. Another method, described in C. K. Crawford in "Charge Neutralization Using Very Low Energy Ions," Scanning Electron Microscopy/1979/II, is to use a beam of very low energy positive ions to neutralize a build-up of negative charges. The ions are generated by a high voltage that ionizes a gas within an ion generator, so the number of ions produced in Crawford's system is determined by factors unrelated to the charge accumulation on the work piece. Such systems were not easy to use because they needed to be balanced for any change in operational conditions, or sample properties. Use of such systems declined with the introduction of low vacuum SEMs and ESEMS and with the increased use of field emission gun SEMs, which allowed satisfactory imaging at lower voltages, thereby reducing work piece charging.

It is a common technique to use a charged particle beam to form an image of the work piece by collecting secondary or back scattered particles emitted as the primary beam scans the work piece surface. The brightness of each point on the image corresponds to the number of secondary particles collected as the beam impacts each point on the substrate. (The term "secondary particle" is used herein to include any particle coming off of the work piece, including back-scattered particles.) Electrical charging of the insulating substrate affects imaging by affecting the paths of secondary particles.

One technique for detecting secondary particles emitted by the impact of a primary electron beam is described in U.S. Pat. No. 4,785,182 to Mancuso, et al., which describes a secondary electron detector for use in an environmental scanning electron microscope ("ESEM"). The detector device consists of an electrode, to which an electrical potential is applied to produce an electric field. Secondary particles emitted at the substrate are accelerated toward the detector and collide with gas molecules, producing additional charged particles, which in turn collide with other gas molecules to produce even more charged particles. Such a process is called a "cascade" effect. The ultimate number of charged particles produced in this manner is proportional to the number of secondary particles emitted at the substrate, thereby producing an amplified signal corresponding to the number of secondary particles. The electron source and much of the path of the primary beam is maintained at a high vacuum by an aperture that passes the primary beam but prevents most gas molecules from entering the column.

In an ESEM detector, the path length of the secondary particles through the detector gas must be sufficiently long to allow enough collisions with gas molecules to provide adequate amplification. To increase the probability of collisions, detectors are typically positioned away from the work piece to provide a relatively long path length as the particles move from the work piece to the detector. Increasing the gas pressure also increases the probability of a collision while traversing a particular path. Gas pressure in an ESEM is typically maintained at around 0.5 to 5 Torr between the work piece and the detector to provide sufficient gas molecules to produce the cascade effect.

Another way of increasing amplification is to provide a magnetic field that causes the particles to move in a curved path or loops within the gas. U.S. Pat. No. 6,184,525 to Van Der Mast describes the use of an electrostatic multipole structure to increase the path length of the secondary electrons to increase the probability of collisions with the gas molecules. Similarly, U.S. Pat. No. 6,365,896 to Van der Mast describes adding an additional magnetic fields between the detector and the specimen holder to lengthen the path of the secondary electrons even further to produce a higher degrees of ionization. Both van der Mast patents are assigned to the assignee of the present application. Japanese Pat. Publication No. 5-174768 also describes an ESEM with a detector positioned in the magnetic field of an objective lens of an electron microscope to increase amplification. Japanese Pat. Publication No. 5-174768 also describes that ions generated by the detector of an environmental scanning electron microscope can neutralize charge build-up on a work piece.

The relatively high gas pressure required for an ESEM detector makes such system unsuitable for use in the same vacuum chamber as another charged particle beam system, such as an ion beam system or a non-ESEM SEM, because most charged particle beam systems cannot operate at the relatively high gas pressures required by an ESEM. The gas molecules interfere with the ions or electrons in the beam, reducing resolution or degrading signal to noise ratio.

SUMMARY OF THE INVENTION

An object of the invention is to provide a system for imaging or processing microscopic structures, and is particularly useful for, though not limited to, imaging or processing microscopic structures on a insulating substrate using a multiple beam system in which at least one column includes an ion generator.

The invention provides a method and apparatus for controlling the electrical surface potential on a substrate, such as a quartz-based lithographic mask, in a charged particle beam system. A preferred embodiment includes an ion generator that uses a gas that is ionized preferably by collisions with secondary charged particles generated by the impact of the primary charged particle beam with the substrate. In some embodiments, the ion generator can be used to provide amplification for a secondary particle signal, such as in an environmental scanning electron microscope. In some embodiments, the ion generator can also be used to provide a gas for chemical assisted charged particle beam etching or deposition. While different embodiments of the invention may be capable of performing charge neutralization, secondary particle signal amplification, supplying gas for gas-assisted charged particle beam operations, and other functions, not all embodiments will provide all functions.

In some embodiments, an ion generator generates ions that neutralize charge on a work piece while maintaining a relatively low gas pressure in the vacuum chamber away from the ion generator. The pressure is sufficiently high at the ion generator to generate ions by collisions of secondary particles with the gas molecules, while being sufficiently low in the remainder of the vacuum chamber so that the time required to evacuate the system to a pressure suitable for operating a non-ESEM charged particle beam system is greatly reduced compared to the time required to evacuate the chamber from the operating pressure of the ESEM.

The foregoing has outlined rather broadly some of the features and technical advantages of various aspects of a preferred system of the present invention in order that the detailed description of the invention that follows may be better understood. Additional features and advantages of the invention will be described hereinafter. It should be appreciated by those skilled in the art that the conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. It should also be realized that while a preferred system for repairing photomasks may implement many of the inventive aspects described below, many of the inventive aspects could be applied independently, or in any combination, depending upon the goals of a specific implementation.

BRIEF DESCRIPTION OF THE DRAWINGS

For a more thorough understanding of the present invention, and the advantages thereof, reference is now made to the following descriptions taken in conjunction with the accompanying drawings, in which:

FIGS. 4A and 4B show electron beam images of a binary mask, FIG. 4A showing an image taken when the mask electrically charged and FIG. 4B showing an image taken the charge neutralized in accordance with an ESEM-type neutralizer.

FIG. 7 shows an embodiment of the invention using an ESEM detector with an immersion lens.

FIG. 10A is a perspective view of one embodiment of an ion generator with a detector.

FIG. 10B is a side sectional view of the ion generator of FIG. 10B.

FIG. 10C is an end sectional view of the ion generator of FIGS. 10A and 10B taken along line 10C—10C in FIG. 10B.

FIG. 10D is an end sectional view of the ion generator of FIGS. 10A and 10B taken along line 10D—10D in FIG. 10B.

DETAILED DESCRIPTION OF THE PREFERRED EMBODIMENTS

Figure 1A:
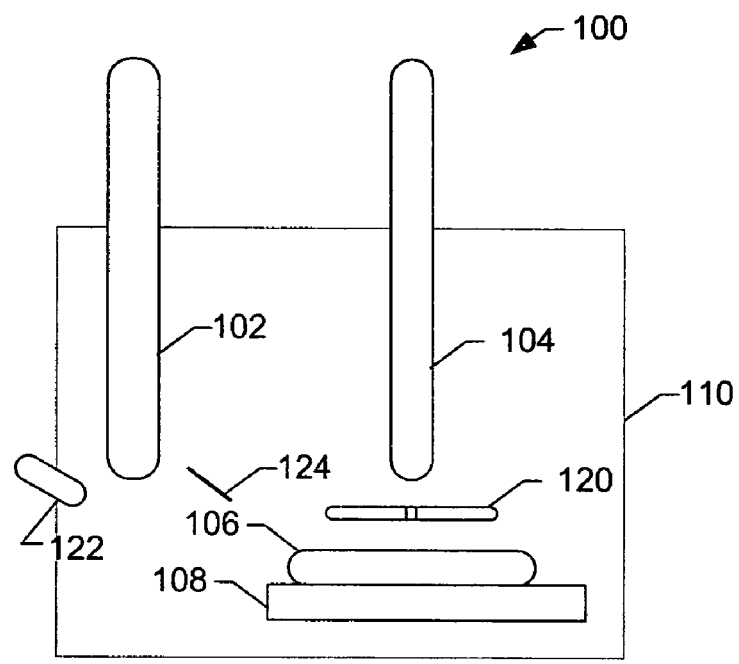
FIG. 1A is a schematic showing a dual beam system embodiment of the invention in which two charged particle beam optical columns are oriented approximately parallel to each other.

A preferred embodiment of the invention uses an ion generator to neutralize negative charge in insulating samples in a charged particle beam system. Because photolithography masks are typically fabricated on an insulating substrate, such as quartz, the invention is useful for charged particle beam operations on photolithography masks.

The ion generator preferably uses secondary or backscattered electrons emanating from the work piece to ionize a gas, in a manner similar to the way a detector works in an environmental scanning electron microscope (ESEM). The secondary particles collide with and ionize the gas molecules as the particles pass through the gas, producing free electrons which then collide with and ionize other gas molecules in a cascading reaction. This ion generation process can generate large quantities of ions for use in stabilizing the charge on insulating samples or for imaging.

By using secondary particles from the work piece to generate the ions, the number of ions generated will be related to the amount of charge impinging on the workpiece from the charged particle beam. Any change in the workpiece potential due the charged particle beam works to automatically regulate the number of ions reaching the work piece. The system can thus provide a self-stabilizing ion generator for neutralizing charge on a work piece in charged particle beam system. Once the gas pressure and ion generator are set-up for controlling the charge, then other microscope parameters, such as beam energy, scan speed, and beam current, can be altered without upsetting the control—the system can be self-regulating.

Some embodiments of the invention use an environmental scanning electron microscope (ESEM) detector, which generates ions to amplify the secondary electron signal, to also provide ions for neutralizing charge on the work piece. Other embodiments of the invention use an ion generator that is a separate device, not connected with an ESEM detector.

Although an ESEM detector generates ions, and those ions can be used for charge neutralization, ESEMs have been unsuitable for use in a multiple beam system, such as a dual beam system including an ESEM and a focused ion beam (FIB) column. ESEMs typically operate at pressures of about 0.5 to 5 Torr, whereas a focused ion beam typically operates at pressures of about $10^{-5}$ Torr. Thus, in a dual beam system containing an ESEM and a focused ion beam column, the user would have to reduce the pressure in the sample vacuum chamber from 0.5 Torr to $10^{-5}$ Torr when switching from using the ESEM to using the FIB. The time required to pump the vacuum chamber down from 0.5 Torr to $10^{-5}$ Torr is a serious disadvantage to using an ESEM together with a FIB in most commercial applications. Even if an ESEM detector uses a gas jet positioned in the detector area, rather than flooding the chamber with the detector gas, the chamber still fills with the detector gas, which must be evacuated before using the ion beam.

Some embodiments of the invention make practical the use of an ESEM and a FIB or SEM in the same vacuum chamber. In some embodiments, the system design tends to localize the gas in a comparatively small volume near the ion generator. In such embodiments, the system maintains a different pressure at different locations in the system so that the gas pressure is higher at the location where ions are to be generated, and lower at other parts of the system so as to reduce interference with the charged particle beams. For example, in one embodiment, when the pressure in a small volume near the ESEM detector is about 0.5 Torr, the background pressure in the chamber is maintained at about $10^{-4}$ Torr. When switching to the FIB, the chamber then only needs to be pumped from $10^{-4}$ Torr to $10^{-5}$ Torr, instead of from 0.5 Torr to $10^{-5}$ Torr. Thus, switching from ESEM operation to FIB operation is much quicker, and a dual beam ESEM-FIB is practical for mask repair and other applications. In some embodiments, it may be possible to operate the ESEM detector or other ion generator and FIB simultaneously.

By returning some of the ions generated by the ESEM detector or other ion generator to the work piece to neutralize charge, the ESEM or other imaging system can produce images that show features on chrome absorbers with a resolution of less than 2 nm. The charge neutralization provided by the ion generator can be controlled in part by controlling the pressure and identity of the gas or gas mixture. The gases or gas mixtures used for ion generation can also be used for charged particle beam assisted etching or deposition to repair defects. The use of gases for etching or deposition in the presence of a charged particle beam is referred to as "beam chemistry." In some embodiments, gases coming from the ion generator for charge neutralization can alternate with different gases for etching or deposition, and in other embodiments gas mixtures may be used.

Different electron final lens configurations will typically require different designs to produce ions for neutralization for secondary particle detection and/or charge neutralization. The several embodiments described below provide example of designs that can be used with different types of electron lenses and, by using these examples and the principles disclosed, skilled persons can design detection/neutralization configurations to work with other types of lenses.

FIG. 1A shows schematically a dual beam system 100 that can be used, for example, for advanced mask repair and metrology and that can incorporate the present invention. The invention is not limited to use in a dual beam system, but can be used in a single beam system or a multiple beam system. System 100 comprises a first charged particle beam column 102 and a second charged particle beam column 104, the axes of columns 102 and 104 being oriented approximately parallel to each other and approximately normal to the surface of a work piece 106. A work piece holder or stage 108 can move the work piece 106 to accurately position it under either column. Columns 102 and 104 and work piece 106 are contained within a vacuum chamber 110.

The invention is not limited to any particular types of columns. For example, an embodiment of the invention could comprise any combination of ion beam columns, such focused beams columns or shaped beam columns, and electron beam columns, such as ESEM and non-ESEM columns. The term ESEM as used herein applies broadly to any electron column configuration that uses the ionization of gas by secondary electrons or backscattered electrons to generate ions for charge neutralization, and/or as part of a detector, while maintaining the electron column at a high vacuum using differential pumping.

FIG. 1A shows, for example, an ESEM detector 120 used with immersion lens column 104 and a separate ion generator 122 used with non-immersion lens column 102 for charge neutralization. Column 102 also includes a non-ESEM secondary particle detector 124, such as a scintillator detector or a channel plate detector. The two electron columns offer different views of the sample. The immersion lens column gives a high resolution image with a symmetrical detector, whereas the non-immersion column allows for detectors that offer a directional component to the image. The ion generator 122 could be replaced with an ESEM detector for both charge neutralization and signal detection. Different implementations could use different combinations of ESEM detectors, non-ESEM detectors, and ion generators.

Figure 1B:
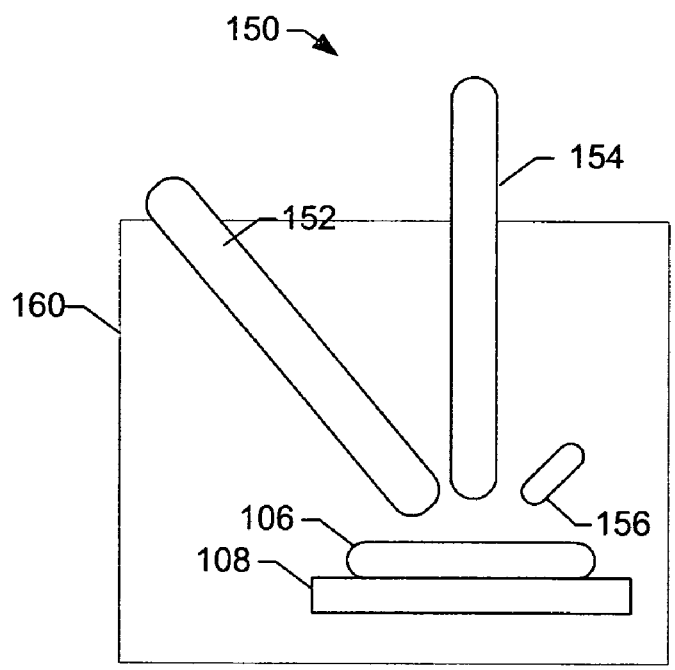
FIG. 1B is a schematic showing a dual beam system embodiment of the invention in which two charged particle beam optical columns are not oriented parallel to each other.

FIG. 1B shows a system 150 in which a first charged particle beam column 152 and a second charged particle beam column 154 are arranged such that their beams are coincident or nearly so. That is, one column is tilted with respect to the other column, so that both beams impact the work piece at the same, or nearly the same, point. If the impact points are offset, work piece holder 108 can move the work piece 106 to accurately position it under the impact point of either column. Columns 152 and 154 and work piece 106 are contained within a vacuum chamber 160. Column 152 and 154 can use any combination of ESEM ion generators, non-ESEM ion generators, and conventional detectors and charge neutralizers, although the tilt of one column may physically make some combinations difficult to implement. FIG. 1B shows a charge generator 156 that provides charge neutralization. Charge generator 156 could be an electron flood gun or an ESEM type ion generator.

At least one of the two columns in a dual beam system used for mask repair is preferably tilted or tiltable with respect to the work piece surface. Using a tilted beam can provide three-dimensional information about the work piece. Three-dimensional information is useful, for example, in the repair of quartz bump defects on a phase shift mask. Such defects, being made of the same material as the substrate, do not exhibit much contrast with the substrate in an image, and so can be difficult to repair without damaging the substrate. U.S. patent application Ser. No. 10/636,309 "Repairing Defects On Photomasks Using A Charged Particle Beam And Topographical Data From A Scanning Probe Microscope," describes a method of using three-dimensional topographical information to repair defects in phase shift masks. A tilted charged particle beam can be used to provide a three-dimensional image instead of the scanning probe microscope described in U.S. patent application Ser. No. 10/636,309. If a charged particle beam system provides the three-dimensional data, it becomes unnecessary to remove the work piece from the vacuum chamber to obtain the information, thereby improving productivity.

Figure 2:
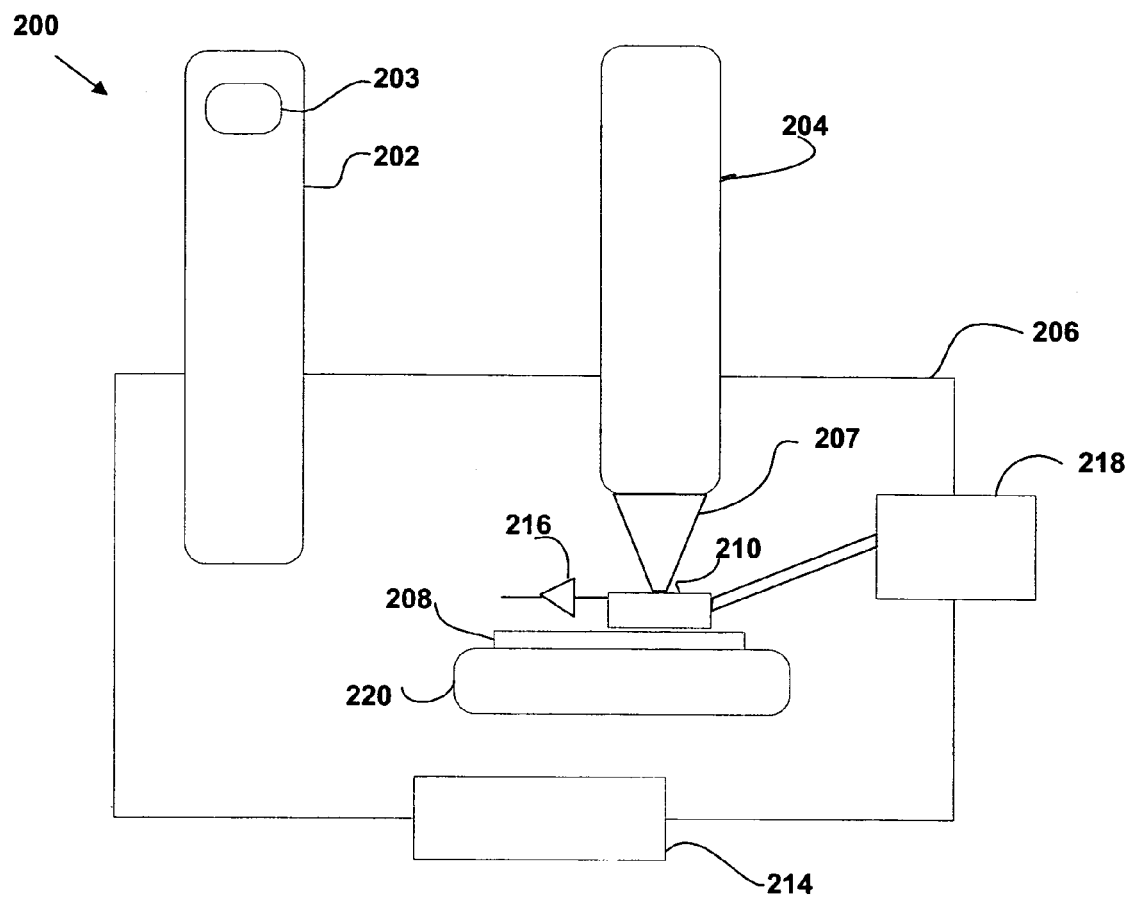
FIG. 2 is a schematic showing an embodiment of the invention that includes a dual beam system when used with an electron column with an immersion magnetic objective lens with an ESEM detector that generates ions.

FIG. 2 shows a system 200 that includes an ion beam column 202 and an environmental scanning electron microscope column 204 positioned within a vacuum chamber 206. Environmental scanning electron microscope column 204 includes a magnetic immersion objective lens 207, which has a high magnetic field at the work piece. Focused ion beam column 202 includes an ion source 203, preferably a gallium liquid metal ion source (LMIS). The invention is not limited to any particular type of ion source, and other ion sources could be used, such as a silicon/gold eutectic LMIS or a plasma ion source. Ion beam column 202 can use a focused beam or a shaped beam. Ion beam column 202 can be used to remove material from the surface of a work piece 208, either by sputtering or by chemical-assisted etching, or to deposit material on the surface of a work piece 208, using ion beam assisted deposition in which a precursor gas is decomposed in the presence of the ion beam to leave a deposit on the surface.

The combination of the large flat detector 210 and the large flat work piece 208 provides some containment for the detector gas, making it possible for a vacuum pump 214 to maintain a pressure between detector 210 and work piece 208 that is several orders of magnitude higher than the general pressure in other parts of chamber 206.

ESEM column 204 includes an ESEM-type detector 210 connected to an amplifier 216 and a gas injector 218 that provides the gas used to amplify the secondary particles emitted from work piece 208. The gas can also be used for chemical assisted electron beam etching or deposition. Stage 220 positions the work piece 208 under either column 202 or column 204, as desired.

Figure 3:
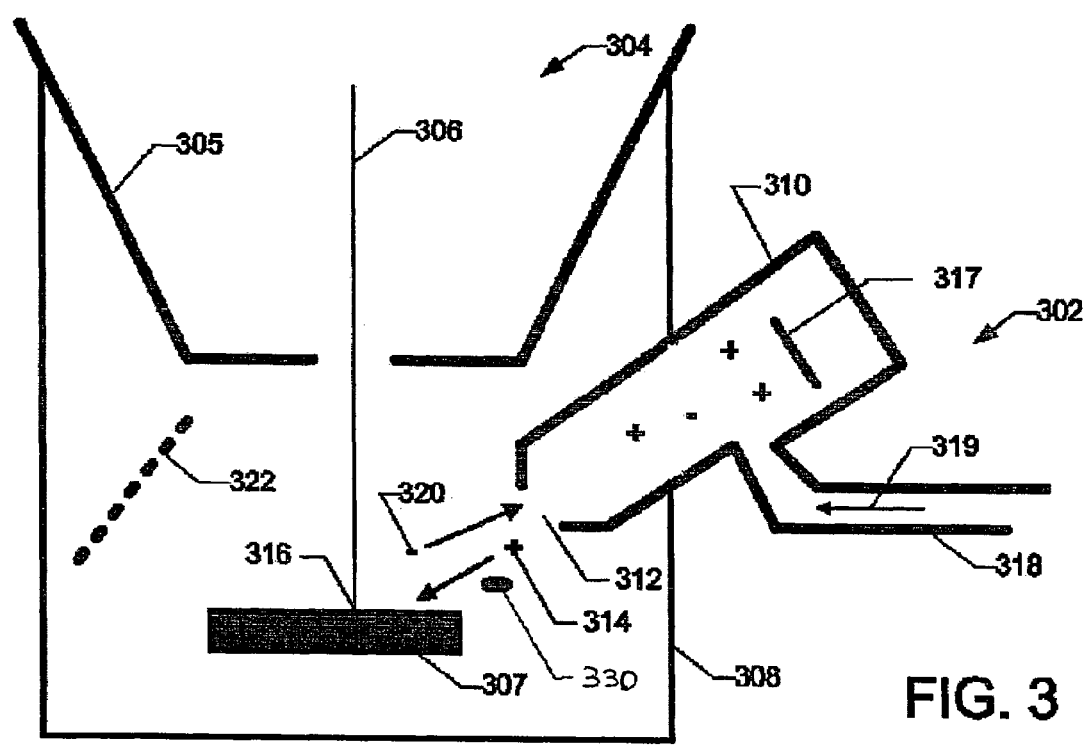
FIG. 3 shows an embodiment of the invention that uses an ion generator for charge neutralization when used with an electron column with a non-immersion magnetic objective lens.

FIG. 3 shows an embodiment of the invention using a self-stabilizing ion generator for neutralizing charge accumulated on the work piece by operation of an electron beam column with a non-immersion lens (i.e., a lens with low magnetic field at the work piece). FIG. 3 shows an electron beam column 304 including a non-immersion objective lens 305 that focuses an electron beam 306 onto the work piece 307, which is enclosed in a system vacuum chamber 308 that may also contain a second charged particle beam column, such as a focused ion beam system.

The ion generator 302 comprises an enclosed tube 310 having an orifice 312 to let ions 314 leave tube 310 to reach impact point 316 where electron beam 306 impacts work piece 307. A high voltage electrode 317 accelerates the secondary particles within tube 310. A pipe 318 brings gas as shown by arrow 319 into tube 310.

The ion generator tube 310 is preferably maintained at a small positive bias voltage, preferably between about 10 V and about 500 V, and typically at about 200 V, to attract some of secondary electrons 320 into the tube. High voltage electrode 317, which is preferably maintained at a potential of between about 300 V and about 2000 V, and typically at about 500 V, further accelerates secondary electrons 320 within tube 310 to trigger gas ionization cascades in tube 310. The ions 314 flow away from the electrode 317 and out of the orifice 312. The positive bias on the tube (and any sample charging) accelerates the ions towards the sample. If there were an excess of ions, the sample would become positively charged, which would reduce the ion flow to the sample and cause the excess ions to flow to the objective lens or back to the tube. Thus, the neutralization is self-regulating. The self regulation may be enhanced by the addition of an electrode 330 which may be grounded or biased to cause the excess ions to flow to the electrode rather than the lens.

The collection and detection of the majority of secondary particles for imaging and analysis can be performed using any conventional high vacuum detector 322, such as a scintillator detector or a channel plate detector. Secondary particles can be collected off-axis near the work piece as shown in FIG. 3 or through the lens. Thus, by using ion generator 302, one can achieve a system that can use non-ESEM detectors, while providing charge neutralization by an ion generator. The vacuum chamber is not flooded with a gas that would preclude operating a non-ESEM-type charged particle beam, either simultaneously or after a relatively brief pump down.

The switchover from using electron column 304 to using an ion beam column (not shown) in chamber 308 can be very quick. The orifice 312 is small enough so that the gas leakage into the system vacuum chamber 308 is small, and gas pressure in chamber 308 can be maintained at a lower level than the pressure in the more open ion generator design of an ESEM detector. To switch from using column 304 to using the ion beam, an operator will typically turn off the gas to the ion generator, and then vent the small ion generator volume to the main chamber. Alternatively, a valve could be placed in orifice 312. In some embodiments, it may be possible to use the ion generator as a gas injector, that is, to direct toward the work piece an etch enhancing gas or a gas that decomposes in the presence of a charged particle beam to deposit a material. Such gases are well known in the art.

A disadvantage of ESEMs is their relatively slow imaging speed, typically less than about 1 microsecond per pixel. By using an ion generator such as ion generator 302, one achieves the benefits of ion generator charge neutralization while being able to use a non-ESEM detector for faster imaging speed. This advantage can also be achieved in a single beam system or a multiple beam system, when at least one column that uses a non-ESEM detector.

Because of the amplification effect of the ion generator, only a relatively small number of secondary particles need to be collected by the ion generator to generate sufficient ions for charge neutralization, and most of the secondary particles are therefore available for collection by the imaging system. When the ion generator is used for charge neutralization and not also as an amplifier for the secondary particle signal, significantly lower amplification can be used. Because the amplification depends on the gas pressure in tube 310, a lower pressure can then be used, which will reduce the pressure in chamber 308.

The appropriate pressure in tube 310 will depend upon the voltage on electrodes inside the ion generator and the number and energy of the captured secondary particles, which factors may vary with the application. To determine an appropriate pressure for a particular embodiment, one can measure the electron signal at the electrode in order to monitor the ion generation and adjust the gas pressure or voltages to achieve sufficient ions to neutralize the substrate. The gas pressure can be reduced in embodiments in which the ions are not used for ESEM-type signal amplification.

Gas pressure in the ion generator 302 is preferably greater than 0.1 Torr and more preferably greater than about 0.3 Torr. A preferred pressure in the tube of about 0.5 Torr would allow a large ion multiplication factor. The pressure is preferably less than 1.0 Torr and more preferably less than 0.7 Torr. An orifice of about 0.2 mm would restrict the gas flow to keep the chamber in the $10^{-5}$ Torr range. The size of the orifice will vary with the system parameters. The orifice should be sufficiently large to allow a significant number of secondary electrons to pass into tube 310 and to allow most of the ions to pass out of the tube 310 orifice. Skilled persons can determine an appropriate orifice size based on the guidance provided above. The pressure in the chamber during operation of the ion generator is preferably less than $10^{-2}$ Torr, more preferably less than 10–3 Torr, more preferably less than about $10^{-4}$ Torr, and most preferably less than or equal to about $10^{-5}$ Torr.

Gases that are known to be suitable for use in ESEM detectors are typically also suitable gases for use with ion generator 302. Desirable properties of suitable gases include low ionization energy, oxidizing, and non-corrosive. For example, water vapor is a suitable detector gas for amplifying the secondary particle signal. Other suitable gases include nitrogen, argon and carbon monoxide. The detector gas can also be mixed with another gas used in charged particle beam assisted deposition or etching. For example, xenon difluoride enhances etching of several materials including silicon. Gas molecules travel to the work piece surface, and, when activated by the charged particle beam, etch the surface. As another example, tungsten hexafluoride and tungsten hexacarbonyl decompose in the presence of an electron beam to deposit tungsten.

In some embodiments, the ion generator in FIG. 3 can be used with an immersion lens. The magnetic field from the lens will normally inhibit the secondary electrons from reaching the ion generator tube. In this case, it is possible place the ion generator in a position such that high energy backscattered electrons (that can escape from the magnetic field) enter the tube and trigger the ion generation process. The magnetic field will not significantly affect the ion flow out. This configuration of ion generator would allow the use of so called "through the lens" detectors that operate in a high vacuum, and are integral with, or above the immersion lens.

FIGS. 4A and 4B show an electron beam image of a binary mask, with FIG. 4A showing the image obtained when the mask is electrically charged due to the electron beam (without any charge neutralization) and FIG. 4B showing the image obtained when the charge on the mask is neutralized in accordance with an embodiment of the invention.

The embodiment of FIG. 3 uses a localized high pressure region in tube 310 for ion generation, so that the vacuum chamber can be maintained at a much lower pressure. The embodiments described below combine the concept of localized high pressure with the use of ESEM detection with immersion lenses. The embodiments described below allow effective electron detection and electron beam charge control while maintaining low chamber pressure, which is preferred for electron beam chemistry and dual beam operation.

Whereas the embodiment of FIG. 3 uses an ion generator that is separate from a detector, the embodiments below use an ion generator that is also used for secondary particle detection. These embodiments allow ESEM-like secondary particle detection, as well as charge control and chemically enhanced charged particle beam operations, particularly when used with a magnetic immersion objective lens. Some embodiments shown provide improved signal amplification and charge control by using a specific combination of a magnetic field and electrostatic field, in conjunction with a gaseous environment. Several such configurations are described in more detail is a U.S. patent application entitled "Particle-optical device and detection means," by Scholtz et al., filed concurrently herewith by the assignee of the present application, and is hereby incorporated by reference.

Japanese Pat. Publication No. 5-174768 shows a column configuration in which a magnetic field from an objective lens is parallel to the electric field, and the application claims that the secondary electrons are trapped around the magnetic flux lines, thereby increasing the path length and amplification. "Particle-optical device and detection means" described above shows that a longer path length can be provided by suitable choice of the electric field shape to implement the so called "magnetic Penning mechanism." This longer path length is in the form of a damped oscillation. One can also configure an electrode such that the electric field includes a component that is orthogonal to the magnetic field. Such a configuration is similar to a structure known as a "magnetron," in which electrons travel in a circular orbit in the presence of a radial electric field perpendicular to a magnetic field. This configuration can greatly extend the electron path length and provide large gaseous amplification in the presence of gas.

Figure 5:
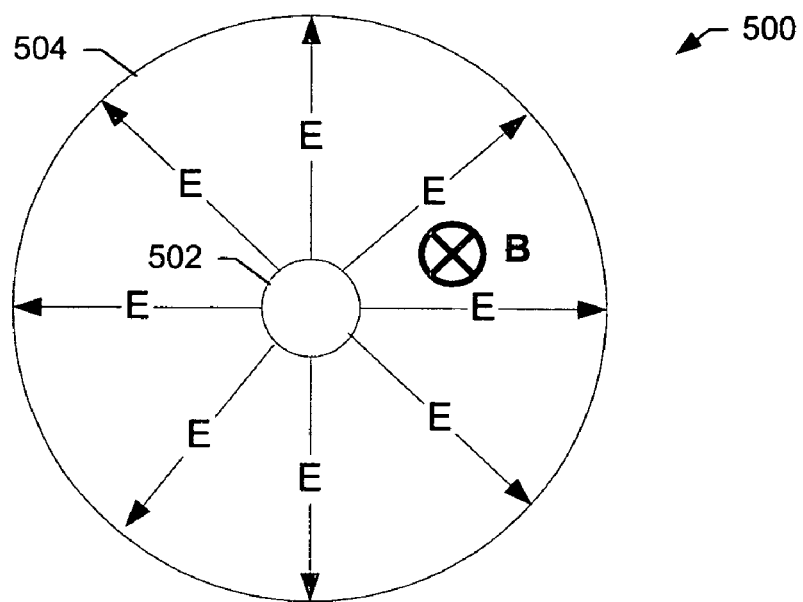
FIGS. 5 and 6 show the magnetic and electric field structure of an ion generator or detector suitable for use with a magnetic immersion lens, and the trajectory of an electron in this field structure
Figure 6:
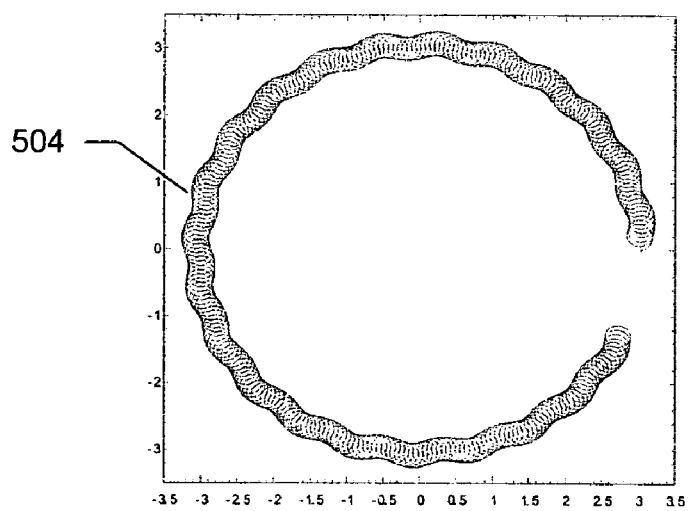

To illustrate the principle, FIG. 5 shows a magnetron structure 500 that consists of two coaxial, cylindrical electrodes, an inner cylinder 502 and an outer cylinder 504. Inner cylinder 502 is grounded, and the outer cylinder 504 is at a positive potential. This potential difference produces a radial electric field between the two electrodes, as illustrated by arrows labeled "E". In addition, there is a magnetic field labeled B, perpendicular to and directed into the plane of the page as indicated by the circled X and preferably uniform throughout the space between the cylinders. An electron that starts at a place between the two electrodes will follow a path similar to that illustrated in FIG. 6.

In a high vacuum, with the right values of electric field (E) and magnetic field (B), the electron can move around the structure indefinitely. However, if there is gas present then the electron will collide with a gas molecule. If the energy of the electron is high enough then the gas molecule may be ionized, and two electrons are then present. These two electrons will start to move further out towards electrode 504 and will then move around electrode 502 in a similar path to FIG. 6, but with a larger radius. These two electrons may further collide with gas molecules to repeat the multiplication process. The increased path length can generate great amplification. It may be shown, however, that the maximum amplification will only occur with the appropriate combinations of the magnetic field, B, and electrostatic field, E.

The combination of the two effects, that is, the magnetic Penning effect from the component of electric field parallel to the magnetic field and the "magnetron" effect from the component of the electric field orthogonal to the magnetic field, creates a greatly enhanced amplification of the signal. To achieve amplification simultaneously using both methods in a single embodiment requires specific combinations of three primary parameters: gas pressure, magnetic field strength, and electric field strength.

FIG. 7 shows an embodiment comprising a charged particle beam system 700 having an immersion lens 702 that focuses an electron beam 704 onto a work piece 706 resting on a stage 708 that rests on a second pole 710 of the immersion lens. System 700 uses as a detector an electrode plate 714 connected to amplifier 716. A pressure limiting aperture 717 maintains a pressure difference between a detection space 718 and the immersion lens 702 by reducing gas flow into the immersion lens 702. Electrode plate 714 is preferably a simple, thin conductive plate having a substantially round central aperture 719 that is substantially coaxial with a magnetic field 722. A positive voltage, in the range of 100 V to 2000 V may be applied to the electrode plate 714 during operation. The bias on electrode plate 714 produces an electric field that, because of aperture 719, is in part parallel, and in part orthogonal to the magnetic field 722 produced by immersion lens 702, and system 700 can therefore achieve secondary particle signal amplification by way of the magnetic Penning and magnetron effects described above.

A large diameter aperture 719 will produce an electric field close to the electrode 714 that is orthogonal to the magnetic field 722, thereby providing a region that can achieve amplification by the magnetron effect. If the hole is too small, however, then the magnetron effect does not occur. If the aperture is too big, however, the enhancement due to the magnetic Penning effect does not occur. Certain hole diameters, together with the certain corresponding values of magnetic field, electric field, and gas pressure, can achieve both amplification mechanisms simultaneously. When these conditions are satisfied, the amplified signal from magnetic Penning mechanism is then compoundly amplified by the magnetron mechanism to achieve a correspondingly large overall amplification.

The amplification of the secondary electron signal also produces positive ions which are needed to avoid the charging of the sample. However, the very large amplification produced by the two mechanism described above may create too many ions. An additional plate 730, which may be grounded, or may be biased, can be provided to collect the excess ions. This plate may also be connected to an amplifier to provide a detected signal.

There are many combinations of hole diameters, magnetic field strengths, electric field strengths, and gas pressures that will achieve the compound mechanism. However, for any specific hole diameter, only certain combinations of bias voltage and magnetic field will produce the compound effect.

Amplification due to the magnetic Penning mechanism will occur only when the peak electric potential along the axis of the electron beam exceeds the ionization potential of the gas. Amplification due to the magnetron effect will only occur if the radial electric field (E) and the magnetic field (B) are such that $2*m*(E/B)^{2/q}$ is greater than the ionization energy of the gas, where m is the mass of an electron and q is the charge of an electron. Skilled persons can use this guidance to determine appropriate diameters for a particular application. As an example, a high amplification of more than 5000 can be provided with an anode hole diameter of 3 mm, anode voltage of 400V, magnetic field of 0.1 Tesla and a pressure of 0.3 Torr of water vapor.

By achieving a large overall amplification, the distance from the work piece to the detector can be kept short, which decreases the working distance of the lens and increases its resolution. Also, the gas pressure at the detector can be reduced, which reduces the overall gas pressure in the chamber, thereby decreasing or eliminating the time required to switch from ESEM operation to FIB or other non-ESEM beam operation. The pressure in detector space 718 can be reduced from about 0.5 Torr to about 0.3 Torr or lower, or even, for some embodiments, to 0.1 Torr or lower. Reducing the gas pressure at the collector further reduces the gas pressure in the vacuum chamber away from the detector.

When the work piece has a suitable shape, for example, a large, flat object, such as a photolithography mask or a semiconductor wafer, and the detector is placed close to the work piece, the geometry provides some confinement to the gas in the area in which amplification occurs. The gas pressure therefore tends to remain greater in the space between the detector and the work piece, and lower in the chamber away from the detector. Some embodiments provide an operating pressure of one or more tenths or a Torr in the amplification zone, while maintaining a reduced pressure in the vacuum chamber in general. Gas pressures in the amplification zone and in the remainder of the vacuum chamber can be similar to those described with respect to the system of FIG. 3, although the chamber pressure will typically be somewhat higher using an ESEM detector, because the gas is less confined.

Thus, the ESEM detector in some embodiments of the invention can operate in a vacuum chamber containing another charged particle beam system, with the detector gas interfering minimally or not at all with the other charged particle beam column, or with the gas pressure in the chamber being raised to an extent at which the chamber can be evacuated relatively quickly to operate the other column.

Figure 8:
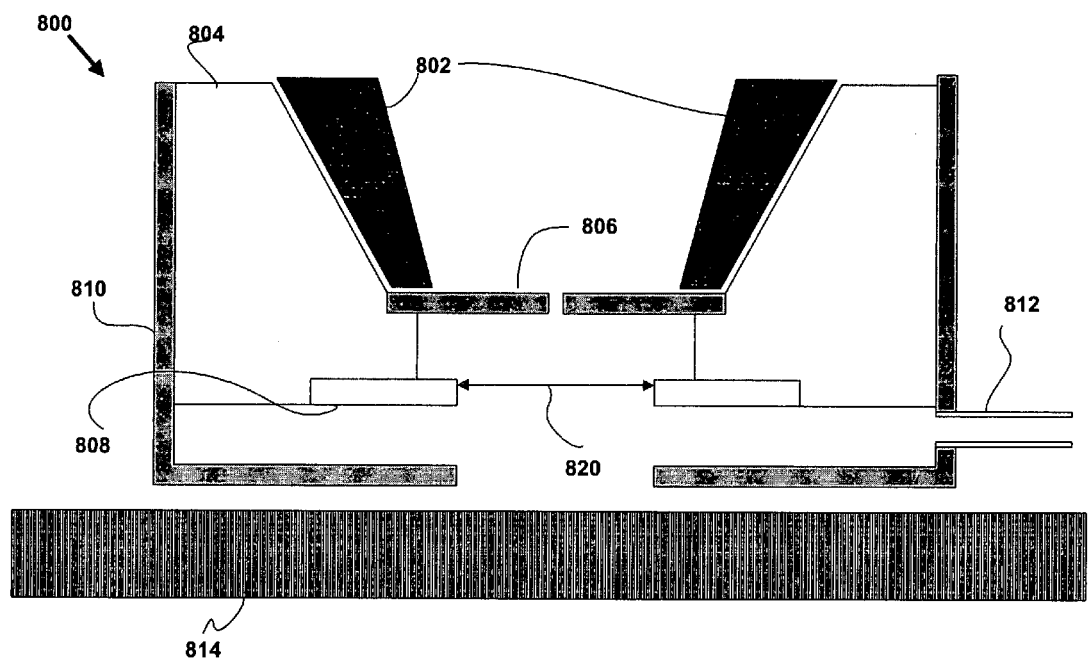
FIG. 8 shows an embodiment of the invention in which a gas passage is incorporated into an ESEM detector with the work piece close to the detector.

The embodiment of FIG. 8 shows a lower potion of an electron beam system 800 that includes a magnetic immersion lens 802 and that uses the secondary particle signal amplification principles described above. System 800 provides enhanced gas isolation to localize the gas and to reduce interference with the operation of other charged particle beam columns in the same vacuum chamber. System 800 includes an insulator 804 that supports a pressure limiting aperture 806 and an annular detector electrode 808. An ion trap 810 surrounds the assembly including the detector electrode 808, the insulator 804, the tip of immersion lens 802, and the pressure-limiting aperture 806. The work piece 814 is placed close to underside of the ion trap. A pipe 812 is used to supply gas into the detection region. A small amount of gas escapes into the electron column through pressure limiting aperture 806, but the flow is low enough that the electron column may be maintained at the required high vacuum level. A small amount of gas also passes between the ion trap and the sample, but the flow is again low enough that the vacuum pump on the sample chamber can maintain a very low gas pressure in the chamber.

A hole 820 in the detector 808 for the gas to exit preferably has a diameter on the order of magnitude of millimeters, depending upon the system parameters. The user alters the magnetic field of the immersion lens when the image is focused. The potential on the detector can then be adjusted, either automatically or manually, to create the required electric field, and optimize the detector gain. Lens 802 provides the required magnetic field in the throughout the detection region.

Typical gaseous detectors use with the magnetic immersion lens perform optimally at a gas pressure of about 0.5 Torr in the chamber and in the path of the primary beam. This embodiment produces the improved signal amplification and charging control described above, but also provides for operation at much lower chamber pressures by concentrating the gas in the region where the amplification occurs. This embodiment is particularly appropriate to the imaging or modification of photomasks or other similar work pieces that are flat, and large in diameter.

Figure 9:
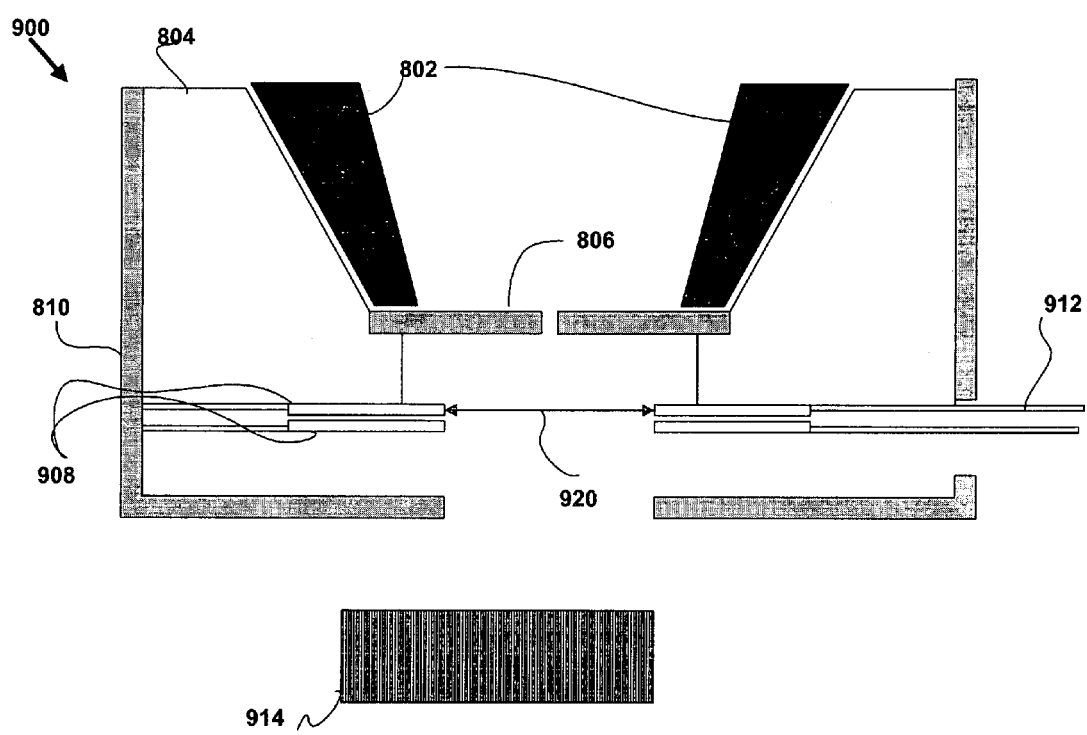
FIG. 9 shows an embodiment of the invention in which a gas passage is incorporated through the anode of an ESEM detector.

The embodiment of FIG. 9 shows a lower potion of an electron beam system 900 that is very similar to that shown in FIG. 8, and similar elements have the same designation. System 900 is more suitable for imaging or modifying of small or irregularly shaped samples. System 900 localizes the gas by a different method. The detector electrode comprises two plates 908, with the gas flowing in between the two plates from an external source through pipe 912. Applicants have found that the main signal amplification and ion generation happens in the region of intense electric field close to the detector electrode. In this embodiment, the electrode is hollow so that gas can be passed through the electrode into the detection region. This creates a high gas pressure close to the electrode, giving high amplification and high ion generation. The gas will then expand into the rest of the region, so that the gas pressure at the beam axis is much lower. This is a major advantage because the gas in the beam path creates a "skirt" of off-axis electrons (particularly at low beam voltages) which have several undesirable results: the off axis electrons create a background signal in the electron image and reduce image contrast; the off-axis electrons will cause etching/deposition outside of the beam impact area in e-beam chemistry. By reducing the gas in the beam path, these undesirable results are reduced or eliminated. Another major advantage of this design for dual beam applications on irregular shaped samples is that the chamber pressure is much lower so that the changeover time between e-beam operation and ion beam operation will be reduced.

In some embodiments, one can shape the detector electrode or the hole in the ion trap or add a bias to the ion trap such as to preferentially control the flow of ions through the hole in the ion trap onto the sample. Embodiments can be used not only to neutralize charge, but also to control an electrical bias on the mask or other work piece. Controlling the bias can provide for optimum imaging and can improve the use of beam chemistry, that is, the use of gases to deposit material or to enhance etching.

The embodiments above described maintain the gas at a sufficient pressure in the ionization region to support adequate ionization by secondary particles, yet maintain the pressure in the rest of the chamber that is either low enough to allow, or be evacuated rapidly to allow, the use of gases directed toward the work piece for charged particle beam deposition or chemically-enhanced charged particle beam etching. The pressure is also low enough in other parts of the vacuum chamber so as to not interfere with the operation of the primary beam columns.

OTHER EMBODIMENTS

FIGS. 10A through 10D show another embodiment of an ion generator for use with non-immersion lens electron columns, such as with the system shown in FIG. 3. The depicted ion generator is capable of both generating and streaming ions onto the sample and detecting secondary electrons for imaging the work-piece. It works well in a dual beam environment where it is desirable to quickly change and/or maintain different pressures both at the work piece, as well as with the gas used for ion generation, electron amplification, or chemical processing. It can also be used in other systems where the maintenance of separate pressures or gas environments is beneficial. Such systems could include but are not limited to SEM, ESEM, FIB and other imaging and charged particle systems.

In the depicted embodiment, the ion generator includes a body 1000 formed from a rear portion 1002 and a forward portion 1004 attached to, but electrically isolated from, each other. These body portions are formed to contain and properly support electrodes, along with the other components described herein. Both rear and forward body portions are typically conductive with the rear portion 1002 set to ground and the forward portion 1004 charged to a reasonably high positive value suitable for attracting secondary work piece electrons to the ion generator. The rear portion 1002 has gas inlet orifice 1003, while the forward portion 1004 has a gas outlet aperture 1005. Orifice 1003 is an unrestricted input for receiving a gas suitable for both ion generation and imaging. Process gasses can also be included in the input gas stream. Aperture 1005 defines an aperture or other restricted opening that limits the flow of imaging gas out of the ion generator 1000 and into the work piece chamber.

The depicted ion generator also includes ion generator cell 1006 formed by detector electrode 1007 and channel electrode 1008. In the depicted embodiment, the detector electrode 1007 is a disk adjacent with, but electrically isolated from, a conically shaped channel electrode 1008. The disk may be perforated to allow gas, from orifice 1003, to more efficiently diffuse within the interior 1010 of the ion generator cell 1006. In the depicted embodiment, the channel electrode 1008 is separate from the forward body portion 1004, but in other embodiments, it could be formed integrally with the forward body portion 1004.

The channel electrode 1008 has a relatively large opening adjacent to detector electrode 1007. It may or may not be sealably connected at this opening with the detector electrode 1007, but it should be electrically isolated from it. At its other end, the channel electrode 1008 has a smaller aperture opening 1009 (next to aperture 1005) for passing charged particles, e.g., electrons (indicated by the "−" character) and positively charged ions (indicated by the "+" character), into and out from the ion generator cell 1006. The interior 1010 of ion generator cell 1006 constitutes a volume of high pressure gas that is used for generating the positively charged ions and amplifying the negatively charged electrons. Depending on desired operational parameters, gas pressure within the interior 1010 may be greater than or equal to the gas pressure outside of the ion generator cell 1006 but still within the ion generator body 1000.

The detector electrode 1007 attracts the electrons toward it inducing gas cascading, which generates the positively charged ions for charge neutralization and free electrons for the amplified image signal. The detector electrode 1007 also collects the electrons for generating the image signal, which is further amplified by amplifier 1017 and sent to an imaging system 1019. It should be recognized, however, that other image detection schemes could be used. For example, other gas cascade techniques such as (1) detecting ions generated in the gas (e.g., as taught in U.S. Pat. No. 4,785,182, incorporated herein by reference), or (2) detecting the light generated in the gas during the cascade process (e.g., as taught in U.S. Pat. No. 4,992,662, incorporated herein by reference) could also be implemented. The channel electrode 1008 is an electrostatic structure that facilitates efficient movement of ions out of the ion generator cell in the direction of the imaged area of the work piece.

The detector electrode 1007 is typically fixed at a fairly high voltage level (e.g., 400 to 1000 volts), while the channel electrode 1008 is typically biased at a lower positive value. Accordingly, an electric field defined by the voltage levels and geometry of the detector and channel electrodes, acts on the charged particles within the ion generator chamber interior 1010. It is normally desirable that proximal to the detector electrode 1007, charged particles are influenced more by the electric field created by the detector electrode 1007 than by the electric field coming from the channel electrode 1008. This can be achieved in a variety of ways. For example, the voltage bias on the channel electrode could vary over the surface of the channel electrode with voltage values being greater on parts of it that are farther away from the detector electrode. Such a non-uniform voltage across the channel electrode 1008 can be obtained by making the channel electrode 1008 from a number of separately biased, electrically isolated electrode pieces. Alternatively, as with the depicted, conically shaped chamber electrode, such a field could also be achieved with a suitably shaped channel electrode 1008 (e.g., having non-uniform radii) to obtain a desired electric field distribution with the channel electrode 1008 biased at a single value that will generally be less than that of the detector electrode 1007).

The depicted ion generator also has an annular magnetic (and/or electro-static) field generating structure 1012 (similar to a lens) substantially coaxially mounted in relation to the ion generator cell 1006 and proximal to the ion generator aperture opening 1005. The magnetic (and/or electro-static) field generating structure 1012 may be controllable for adjusting the generated field in order to funnel electrons through the aperture opening 1005 and into the ion generator cell 1006. Also included in the depicted embodiment is an electrode 1014 (which may be annular) to control the number and/or concentration of ions that ultimately impinge on the imaged area of the work piece. These structures may be either integrated into, or independent of, the ion generator body. This will depend on the particular application and on the geometries and biasing of the ion generator body 1000 and ion generator cell 1006. Along with these structures, adjusting the imaging gas pressure in the ion generator cell 1006 can also be used to control the number and concentration of ions supplied to the imaged area of the work piece.

Figure 11:
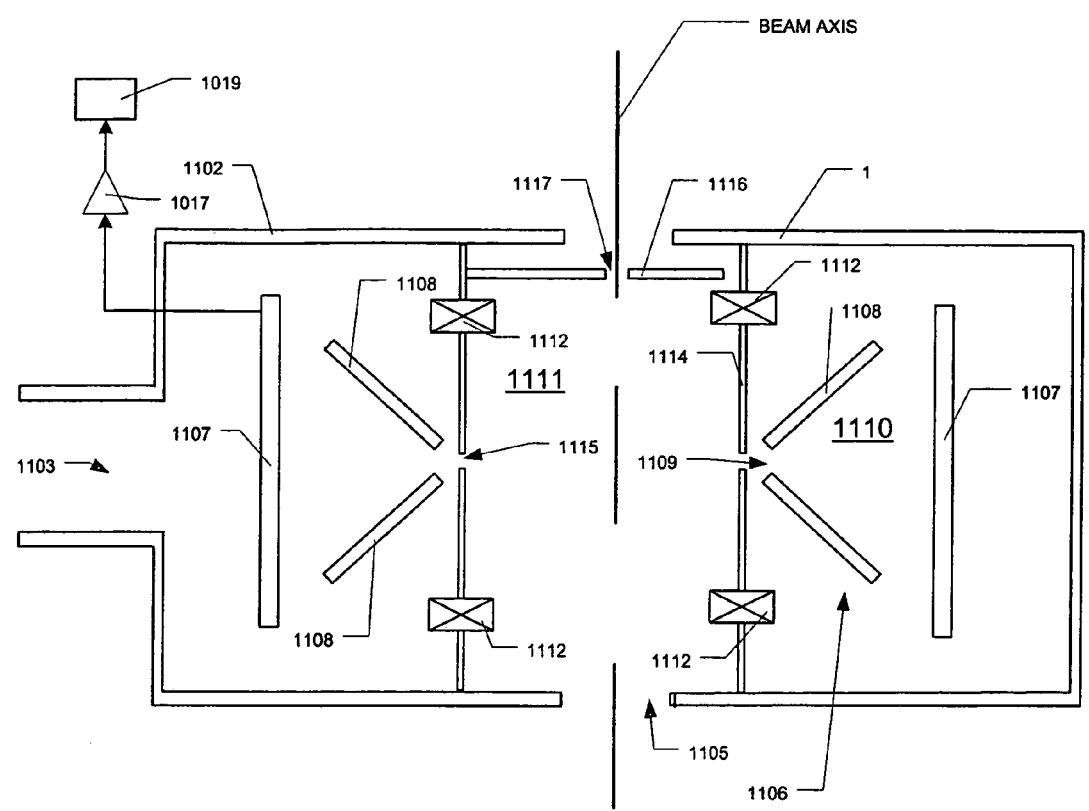
FIG. 11 is a side sectional view of an on-axis embodiment of an ion generator with a detector.

FIG. 11 shows an on-axis version of the off-axis ion generator of FIGS. 10A through 10D with corresponding components numbered similarly. The ion generator of FIG. 11 operates similarly to the off-axis embodiment but with the following exceptions. Ion generator 1100 includes an additional upper disk electrode 1116 with an aperture opening 1117 for passing the charged particle beam. This electrode, like detector electrode 1107 and channel electrode 1108 is positively biased to attract electrons from the work piece up through ion generator opening 1105 into the low pressure bean space 1111 and force positively charged ions out of opening 1105 and onto the work piece. The cylindrical electrode 1114 has an annular slit opening 1115 that passes both electrons into ion generator cell 1106 through annular slit opening 1109 and ions out into the low pressure, beam space 1111. When electrons in the beam space 1111 get close to annular slit opening 1115, they become more influenced by detector electrode 1107 and channel electrode 1108, which causes them to enter the opening and pass into the ion generator cell 1106 resulting in ion generation and electron image signal amplification for electrons impinging upon detector electrode 1107. Conversely, electro-static forces dominated by detector electrode 1107 and channel electrode 1108 force ions out of the ion generator cell 1106 through openings 1109 and 1115 and into the beam space 1111. Once there, forces exerted from disk electrode 1116 dominate, causing the ions to pass out of opening 1105 and onto the work piece. In this embodiment, cylindrical electrode 1114 serves as a gas pressure barrier between the low pressure beam space 1111 and inner, high pressure ion generator space 1110, but may also be biased to assist with the control of the flow of ions and electrons.

Although the invention is not limited to any particular application, some embodiments are particularly useful for repairing lithography masks, especially masks used for the 70 nm lithography node and beyond, including optical, x-ray, extreme ultra violet (EUV), different absorbers, and alternating phase shift masks (APSM) technologies.

Also, while the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A charged particle beam apparatus comprising:
 a work piece vacuum chamber for containing a work piece and having a background chamber pressure;
 a charged particle beam source;
 a charged particle beam optical column for directing a particle beam along an optical axis toward the work piece;
 a charged particle detector comprising a volume including a detector gas ionizable by the charged particles, electrodes to produce an electric field to cause the ionization to take place, and a detector plate to detect signals induced in the ionized gas, the charged particle detector including a passage for delivery of the detector gas to maintain the pressure of the detector gas around the detector sufficient to operate the detector, while maintaining the pressure in the work piece vacuum chamber at a significantly lower pressure.

2. The apparatus of claim 1 in which the charged particle beam column comprises a scanning electron microscope column.

3. The apparatus of claim 1 in which the charged particle detector comprises two plates, each plate having an aperture co-axial with the optical axis.

4. The apparatus of claim 3 in which the gas passes in between the two plates.

5. The apparatus of claim 1 in which the passage for delivery of gas comprises a nozzle directing gas toward a region between the detector plate and a work piece position.

6. A charged particle beam apparatus comprising:
a work piece vacuum chamber for containing a work piece and having a background chamber pressure
a charged particle beam source;
a charged particle beam optical column for directing a particle beam along an optical axis toward the work piece;
an ion generator in which secondary particles generated by the impact of charged particle beam on a work piece or particles from the primary beam backscattered by the work piece ionize an ion producing gas, the ion generator positioned such that at least some of the ions travel to work piece to neutralize charge on the work piece, the ion generator including a chamber containing a gas, the chamber connected to the work piece vacuum chamber though an aperture that allows secondary or backscattered particles from the work piece to enter the chamber and allows ions to exit the chamber to neutralize charge on the work piece.

7. The charged particle beam apparatus of claim 6 in which the charged particle beam optical column includes an objective lens and an optical axis and in which ion generator is positioned such that a line drawn from the center of the aperture to the intersection of the optical axis with the work piece is not parallel to the optical axis.

8. The charged particle beam apparatus of claim 6 in which the charged particle beam optical column comprises a scanning electron microscope column.

9. A charged particle beam apparatus comprising:
a work piece vacuum chamber for containing a work piece and having a background chamber pressure
a charged particle beam source;
a charged particle beam optical column for directing a particle beam toward the work piece;
an ion generator in which secondary particles generated by the impact of charged particle beam on a work piece or particles from the primary beam backscattered by the work piece ionize an ion producing gas, the ion generator positioned such that at least some of the ions travel to work piece to neutralize charge on the work piece, the ion generator configured such that the ion producing gas is maintained at a sufficiently high pressure at the ion generator to produce sufficient ions from the secondary or backscattered particles to neutralize charge accumulation on the work piece, while the background chamber pressure remains at a significantly lower pressure.

10. The charged particle beam apparatus of claim 9 in which the ion producing gas is maintained at a pressure greater than about 0.1 Torr and in which the background chamber pressure is maintained at a pressure of less than about 0.01 Torr.

11. The charged particle beam apparatus of claim 9 in which the ion producing gas is maintained at a pressure greater than about 0.3 Torr and in which the background chamber pressure is maintained at a pressure of less than about $10^{-3}$ Torr.

12. The charged particle beam apparatus of claim 9 in which the ion producing gas is maintained at a pressure greater than about 0.4 Torr and in which the background chamber pressure is maintained at a pressure of less than about $10^{-3}$ Torr.

13. The charged particle beam apparatus of claim 9 in which the ion generator comprises an a particle detector using gas ionization amplification.

14. The charged particle beam apparatus of claim 13 in which the particle detector comprises a plate having an aperture co-axial with the charged particle beam.

15. The charged particle beam apparatus of claim 14 in which the charged particle beam column includes a magnetic immersion objective lens and in which the detector plate is positioned above a work piece position and below a pole of the magnetic immersion objective lens.

16. The charged particle beam apparatus of claim 13 in which the particle detector includes a passage for transporting the ion producing gas.

17. The charged particle beam apparatus of claim 9 in which the charged particle beam includes an objective lens and an optical axis and in which ion generator is positioned such that a line drawn from the center of the aperture to the intersection of the optical axis with the work piece is not parallel to the optical axis.

18. The charged particle beam apparatus of claim 9 in which the ion generator comprises a chamber containing a gas, the chamber communicating to the work piece vacuum chamber though an aperture that allows secondary particles from the work piece to enter the chamber and allows ions to exit the chamber to neutralize charge on the work piece.

19. The charged particle beam apparatus of claim 9 in which the ion producing gas increases the etch rate of charged particle beam or decomposes in the presence of the charged particle beam to deposit a material on the work piece.

20. The charged particle beam apparatus of claim 9, further comprising: a second charged particle beam source; and a second charged particle beam column for directing a second beam of charged particles toward a work piece positioned in the work piece vacuum chamber, a detector for detecting charged particles emitted from the work piece upon impact of particles in the second charged particle beam, the pressure in the work piece vacuum chamber being sufficiently low to operate the second charged particle beam column.

21. An ion generator for controlling charge on a sample that produces secondary electrons as it is being worked on in a sample chamber, comprising:
a body having rear and forward ends and a gas inlet opening to be controllably supplied with a gas, the forward end having an aperture opening to receive the secondary electrons and to emit positively charged ions;
a detector electrode mounted within said body; and
a channel electrode mounted within the body between the detector electrode and the aperture opening to channel the secondary electrons toward the detector electrode, the channel and detector electrodes defining an inner volume, wherein the body is configured to maintain the supplied gas at least within the inner volume at a working pressure sufficiently higher than that of the sample chamber to promote gas ionization cascades thereby generating positively charged ions to be emitted from the inlet opening and providing an amplified secondary electron signal to the detector electrode.

22. The ion generator of claim 21, wherein the channel electrode is formed as part of the body.

23. The ion generator of claim 21, wherein the channel electrode is conical in shape.

24. The ion generator of claim 21, wherein the channel and detector electrodes are electrically isolated from one another.

25. The ion generator of claim 21, wherein the channel electrode further comprises a plurality of discretely biased electrode components.

26. The ion generator of claim 21, further comprising a controllable magnetic field generation structure proximal to the aperture opening for guiding secondary electrons into the aperture opening.

* * * * *